United States Patent [19]

Gehring et al.

[11] Patent Number: 4,685,956
[45] Date of Patent: Aug. 11, 1987

[54] 1-ARYL-5-HYDRAZINO-PYRAZOLES, COMPOSITIONS CONTAINING THEM, AND HERBICIDAL METHOD OF USING THEM

[75] Inventors: Reinhold Gehring, Wuppertal; Otto Schallner, Monheim; Jörg Stetter, Wuppertal; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 885,051

[22] Filed: Jul. 14, 1986

[30] Foreign Application Priority Data

Aug. 8, 1985 [DE] Fed. Rep. of Germany ....... 3528478

[51] Int. Cl.⁴ .................. A01N 43/56; C07D 231/38; C07D 401/04
[52] U.S. Cl. ........................ 71/92; 540/597; 540/598; 540/603; 544/82; 544/130; 544/140; 546/187; 546/211; 546/279; 548/362; 548/374; 548/376; 548/377
[58] Field of Search ............... 546/279, 187, 211; 548/362, 376, 377, 374; 71/92; 540/597, 598, 603; 544/82, 130, 140

[56] References Cited

U.S. PATENT DOCUMENTS 4,459,150 7/1984 Hatton et al. .................. 548/362

OTHER PUBLICATIONS

Hetarylpyrazoles., IV(1), Mar.–Apr. 1983, 277–279, J. Het. Chem. 20.

Primary Examiner—Henry R. Jiles
Assistant Examiner—Kurt G. Briscoe
Attorney, Agent, or Firm—Sprung Horn Kramer & Woods

[57] ABSTRACT

Herbicidally active 1-aryl-5-hydrazinopyrazoles of the formula

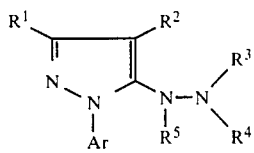

in which
$R^1$ represents hydrogen or alkyl,
$R^2$ represents cyano or nitro,
$R^3$ represents hydrogen, or represents in each case optionally substituted alkyl, alkenyl, alkinyl or cycloalkyl, or represents a radical

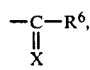

or represents a radical $-SO_2-R^7$,
$R^4$ represents hydrogen, or represents in each case optionally substituted alkyl, alkenyl, alkinyl or cycloalkyl, or represents a radical

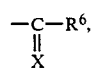

or represents a radical $-SO_2-R^7$,
$R^5$ represents hydrogen: or, in the case where $R^4$ represents hydrogen, also represents a radical

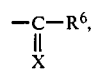

or represents a radical $-SO_2-R^7$, or represents in each case optionally substituted alkyl, alkenyl, alkinyl or cycloalkyl, wherein, in each case,
X represents oxygen or sulphur,
$R^6$ represents hydrogen, alkyl, alkoxy, alkoxyalkyl, alkylthio, alkylthioalkyl, alkylamino, dialkylamino, halogenoalkyl, alkenyl or alkinyl, or represents optionally substituted cycloalkyl, or represents in each case optionally substituted aryl, aryloxy, arylthio or arylamino and
$R^7$ represents alkyl, hydroxyalkyl, alkoxyalkyl, halogenoalkyl, alkenyl, alkinyl or cycloalkyl, or represents in each case optionally substituted aralkyl or aryl and
Ar represents substituted phenyl, or represents optionally substituted pyridyl.

7 Claims, No Drawings

1-ARYL-5-HYDRAZINO-PYRAZOLES, COMPOSITIONS CONTAINING THEM, AND HERBICIDAL METHOD OF USING THEM

The invention relates to new 1-aryl-5-hydrazinopyrazoles, several processes for their preparation and their use as herbicides.

It is already known that certain 1-aryl-pyrazoles, such as, for example, 4-cyano-5-propionamido-1-(2,4,6-tri- chlorophenyl)-pyrazole, have herbicidal properties (compare, for example, DE-OS (German Published Specification) No. 3,226,513).

However, the herbicidal activity of these already known compounds towards harmful plants, like their tolerance towards important crop plants, is not always completely satisfactory in all fields of use.

Furthermore hetarylpyrazoles, such as for example, 3-methyl-4-nitro-1-phenyl-5-hydrazino-pyrazole, are known (J.Het.Chem. 20,277-279 (1983)). However, a use of these compounds in particular in the field of agriculture is not mentioned.

New 1-aryl-5-hydrazino-pyrazoles of the general formula (I)

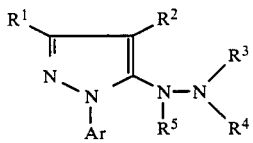

in which
  $R^1$ represents hydrogen or alkyl,
  $R^2$ represents cyano or nitro,
  $R^3$ represents hydrogen, or represents in each case optionally substituted alkyl, alkenyl, alkinyl or cycloalkyl, or represents a radical

or represents a radical $-SO_2-R^7$,
  $R^4$ represents hydrogen, or represents in each case optionally substituted alkyl, alkenyl, alkinyl or cycloalkyl, or represents a radical

or represents a radical $-SO_2-R^7$,
  $R^5$ represents hydrogen; or, in the case where
  $R^4$ represents hydrogen, $R^5$ may also represent a radical

or a radical $-SO_2-R^7$, or may represent in each case optionally substituted alkyl, alkenyl, alkinyl or cycloalkyl,
wherein, in each case,
  X represents oxygen or sulphur,
  $R^6$ represents hydrogen, alkyl, alkoxy, alkoxyalkyl, alkylthio, alkylthioalkyl, alkylamino, dialkylamino, halogenoalkyl, alkenyl or alkinyl, or represents optionally substituted cycloalkyl, or represents in each case optionally substituted aryl, aryloxy, arylthio or arylamino and
  $R^7$ represents alkyl, hydroxyalkyl, alkoxyalkyl, halogenoalkyl, alkenyl, alkinyl or cycloalkyl, or represents in each case optionally substituted aralkyl or aryl and
  Ar represents substituted phenyl, or represents optionally substituted pyridyl, have now been found.

It has furthermore been found that the new 1-aryl-5-hydrazino-pyrazoles of the general formula (I)

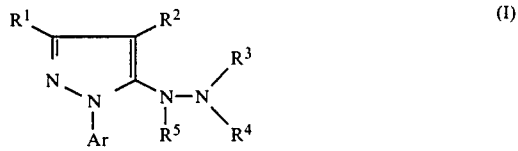

in which
  $R^1$ represents hydrogen or alkyl,
  $R^2$ represents cyano or nitro,
  $R^3$ represents hydrogen, or represents in each case optionally substituted alkyl, alkenyl, alkinyl or cycloalkyl, or represents a radical

or represents a radical $-SO_2-R^7$,
  $R^4$ represents hydrogen, or represents in each case optionally substituted alkyl, alkenyl, alkinyl or cycloalkyl, or represents a radical

or represents a radical $-SO_2-R^7$,
  $R^5$ represents hydrogen; or, in the case where
  $R^4$ represents hydrogen, $R^5$ may also represent a radical

or a radical $-SO_2-R^7$, or may represent in each case optionally substituted alkyl, alkenyl, alkinyl or cycloalkyl,
wherein, in each case,
  X represents oxygen or sulphur,
  $R^6$ represents hydrogen, alkyl, alkoxy, alkoxyalkyl, alkylthio, alkylthioalkyl, alkylamino, dialkylamino, halogenoalkyl, alkenyl or alkinyl, or represents optionally substituted cycloalkyl, or represents in each case optionally substituted aryl, aryloxy, arylthio or arylamino and
  $R^7$ represents alkyl, hydroxyalkyl, alkoxyalkyl, halogenoalkyl, alkenyl, alkinyl or cycloalkyl, or represents in each case optionally substituted aralkyl or aryl and
  Ar represents substituted phenyl, or represents optionally substituted pyridyl, are obtained by a process in which
(a) 1-aryl-5-halogeno-pyrazoles of the formula (II)

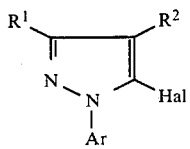

in which
R[1], R[2] and Ar have the abovementioned meaning and Hal represents halogen, are reacted with hydrazine derivatives of the formula (III)

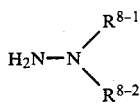

in which
R[8-1] and R[8-2] independently of one another in each case represent hydrogen, or represent in each case optionally substituted alkyl, alkenyl, alkinyl or cycloalkyl,
if appropriate in the presence of a diluent, or in which
(b) the 5-hydrazino-1-aryl-pyrazoles obtainable by process (a), of the formula (Ia)

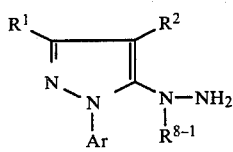

in which
R[1], R[2], R[8-1] and Ar have the abovementioned meaning,
or of the formula (Ib)

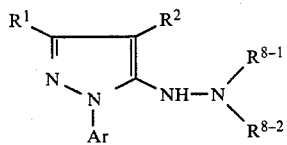

in which
R[1], R[2], R[8-1], R[8-2] and Ar have the abovementioned meaning,
(α) are reacted with alkylating agents of the formula (IV)

$$R^{8-3}-A^1 \quad (IV)$$

in which
R[8-3] represents in each case optionally substituted alkyl, alkenyl, alkinyl or cycloalkyl and A[1] represents an electron-withdrawing leaving group,
or
(β) are reacted with acylating agents of the formula (V)

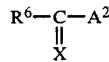

in which
R[6] and X have the abovementioned meaning and

A[2] represents an electron-withdrawing leaving group,
or
(γ) are reacted with iso(thio)cyanates of the formula (VI)

$$R^{6-1}-N=C=X \quad (VI)$$

in which
R[6-1] represents alkyl, or represents optionally substituted aryl and
X has the abovementioned meaning,
or
(δ) are reacted with sulphonylating agents of the formula (VII)

$$R^7-SO_2-A^3 \quad (VII)$$

in which
R[7] has the abovementioned meaning and
A[3] represents an electron-withdrawing leaving group,
in each case if appropriate in the presence of a diluent and if appropriate in the presence of an acid-binding agent or reaction auxiliary.

Finally, it has been found that the new 1-aryl-5-hydrazino-pyrazoles of the formula (I) have herbicidal properties.

Surprisingly, the 1-aryl-5-hydrazino-pyrazoles of the formula (I) according to the invention have a better herbicidal activity against harmful plants, at the same time coupled with a better tolerance towards important useful plants, than, for example, the compound 4-cyano-5-propionamido-1-(2,4,6-trichlorophenyl)-pyrazole, which is known from the prior art and is a closely related compound chemically and from the point of view of its action.

Formula (I) provides a general definition of the 1-aryl-5-hydrazino-pyrazoles according to the invention.
Preferred compounds of the formula (I) are those in which
R[1] represents hydrogen, or represents straight-chain or branched alkyl with 1 to 4 carbon atoms,
R[2] represents cyano or nitro,
R[3] represents hydrogen, or represents alkyl, alkenyl or alkinyl with in each case up to 8 carbon atoms and in each case optionally monosubstituted or polysubstituted by identical or different substituents, possible substituents in each case being: halogen, cyano, nitro, hydroxyl, carboxyl, in each case straight-chain or branched alkoxy and alkoxycarbonyl with in each case 1 to 6 carbon atoms in the alkyl part and aminocarbonyl which is optionally substituted by alkyl, alkoxy, alkylsulphonyl, alkenyl or alkinyl with in each case up to 4 carbon atoms, it also being possible for the nitrogen atom of the aminocarbonyl radical to be part of a saturated 3-membered to 7-membered heterocyclic radical which can optionally also contain 1 or 2 further heteroatoms, in particular nitrogen, oxygen or sulphur; or furthermore represents cycloalkyl which has 3 to 7 carbon atoms and is optionally monosubstituted or polysubstituted by identical or different substituents from the group comprising halogen and/or straight-chain or branched alkyl with 1 to 4 carbon atoms, or represents a radical

or represents a radical $SO_2$—$R^7$, $R^4$ represents hydrogen, or represents alkyl, alkenyl or alkinyl with in each case up to 8 carbon atoms and in each case optionally monosubstituted or polysubstituted by identical or different substituents, possible substituents in each case being: halogen, cyano, nitro, hydroxyl, carboxyl, in each case straight-chain or branched alkoxy and alkoxycarbonyl with in each case 1 to 6 carbon atoms in the alkyl part and aminocarbonyl which is optionally substituted by alkyl, alkoxy, alkylsulphonyl, alkenyl or alkinyl with in each case up to 4 carbon atoms, it also being possible for the nitrogen atom of the aminocarbonyl radical to be part of a saturated 3-membered to 7-membered heterocyclic radical, which can optionally also contain 1 or 2 further heteroatoms, in particular nitrogen, oxygen or sulphur; or furthermore represents cycloalkyl which has 3 to 7 carbon atoms and is optionally monosubstituted or polysubstituted by identical or different substituents from the group comprising halogen and straight-chain or branched alkyl with 1 to 4 carbon atoms, or represents a radical

or represents a radical $SO_2$—$R^7$, $R^5$ represents hydrogen; or, in the case where $R^4$ represents hydrogen, $R^5$ may also represent a radical

or a radical —$SO_2$—$R^7$ or may represent alkyl, alkenyl or alkinyl with in each case up to 8 carbon atoms and in each case optionally monosubstituted or polysubstituted by identical or different substituents, possible substituents in each case being: halogen, cyano, nitro, hydroxyl, carboxyl, in each case straight-chain or branched alkoxy and alkoxycarbonyl with in each case up to 6 carbon atoms in the alkyl part and aminocarbonyl which is optionally substituted by alkyl, alkoxy, alkylsulphonyl, alkenyl or alkinyl with in each case up to 4 carbon atoms, it also being possible for the nitrogen atom of the aminocarbonyl radical to be part of a saturated 3-membered to 7-membered heterocyclic radical which can optionally contain 1 or 2 further heteroatoms, in particular nitrogen, oxygen or sulphur; or furthermore represents cycloalkyl which has 3 to 7 carbon atoms and is optionally monosubstituted or polysubstituted by identical or different substituents from the group comprising halogen and straight-chain or branched alkyl with 1 to 4 carbon atoms, wherein, in each case, X represents oxygen or sulphur, $R^6$ represents hydrogen, or represents in each case straight-chain or branched alkyl, alkoxy, alkoxyalkyl, alkylthio, alkylthioalkyl, alkylamino or dialkylamino with in each case 1 to 4 carbon atoms in the individual alkyl parts, or represents straight-chain or branched halogenoalkyl with 1 to 4 carbon atoms and 1 to 9 identical or different halogen atoms, or represents in each case straight-chain or branched alkenyl or alkinyl with 2 to 4 carbon atoms, or represents cycloalkyl which has 3 to 7 carbon atoms and is optionally monosubstituted or polysubstituted by identical or different substituents from the group comprising halogen and in each case straight-chain or branched alkyl with 1 to 4 carbon atoms and halogenoalkyl with 1 to 4 carbon atoms and 1 to 9 identical or different halogen atoms, or represents phenyl, phenoxy, phenylthio or phenylamino, in each case optionally monosubstituted or polysubstituted by identical or different substituents, the phenyl substituents selected in each case being: halogen or in each case straight-chain or branched alkyl, alkoxy, with in each case 1 to 4 carbon atoms, or halogenoalkyl with 1 to 4 carbon atoms and 1 to 9 identical or different halogen atoms and $R^7$ represents in each case straight-chain or branched alkyl, hydroxyalkyl or alkoxyalkyl with in each case 1 to 4 carbon atoms in the individual alkyl parts, or represents straight-chain or branched halogenoalkyl with 1 to 4 carbon atoms and 1 to 9 identical or different halogen atoms, or represents in each case straight-chain or branched alkenyl or alkinyl with in each case 2 to 4 carbon atoms, or represents cycloalkyl with 3 to 7 carbon atoms, or represents benzyl or phenyl, in each case optionally monosubstituted or polysubstituted by identical or different substituents from the group comprising halogen, cyano, nitro and in each case straight-chain or branched alkyl, alkoxy and alkylthio with in each case 1 to 4 carbon atoms and halogenoalkyl with 1 to 4 carbon atoms and 1 to 9 identical or different halogen atoms and Ar represents phenyl which is monosubstituted or polysubstituted by identical or different substituents, or represents 2-pyridyl, 3-pyridyl or 4pyridyl, in each case optionally monosubstituted or polysubstituted by identical or different substituents, possible substituents in each case being: cyano, nitro, halogen, in each case straight-chain or branched alkyl, alkoxy or alkoxycarbonyl with in each case 1 to 4 carbon atoms in the alkyl part, in each case straight-chain or branched halogenoalkyl or halogenoalkoxy with in each case 1 to 4 carbon atoms and 1 to 9 identical or different halogen atoms and a radical —$S(O)_m$—$R^9$, wherein $R^9$ represents amino, or represents in each case straight-chain or branched alkyl, alkylamino or dialkylamino with in each case 1 to 4 carbon atoms in the individual alkyl parts or halogenoalkyl with 1 to 4 carbon atoms and 1 to 9 identical or different halogen atoms and m represents the number 0, 1 or 2.

Particularly preferred 1-aryl-5-hydrazino-pyrazoles of the general formula (I) are those in which $R^1$ represents hydrogen, methyl, ethyl, n- or i-propyl, or n-, i-, s- or t-butyl, $R^2$ represents cyano or nitro, $R^3$ represents hydrogen, or represents methyl, ethyl, n- or i-propyl, n-, i-, s- or t-butyl, allyl, butenyl, propargyl or butinyl, in each case optionally mono-, di- or trisubstituted by identical or different substituents, possible substituents in each case being: fluorine, chlorine, bromine, iodine, cyano, nitro, hydroxyl, carboxyl, methoxy, ethoxy, n- or i-propoxy, methoxycarbonyl, ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N-methyl-N-ethylaminocarbonyl, N-methyl-N-propylaminocarbonyl, N-ethyl-N-propylaminocarbonyl, N-methyl-N-methoxyaminocarbonyl, N,N-diallylaminocarbonyl, N-methyl-N-propargylaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl; or furthermore represents cyclopropyl, cyclopentyl, cyclohexyl or cycloheptyl, in each case optionally mono-, di-, tri-, tetra- or pentasubstituted by identical or different substituents from the group comprising chlorine, methyl or ethyl, or represents a radical

or represents a radical —SO$_2$—R$^7$,

R$^4$ represents hydrogen, or represents methyl, ethyl, n- or i-propyl, n-, i-, s- or t-butyl, allyl, butenyl, propargyl or butinyl, in each case optionally mono-, di- or trisubstituted by identical or different substituents, possible substituents in each case being: fluorine, chlorine, bromine, iodine, cyano, nitro, hydroxyl, carboxyl, methoxy, ethoxy, n- or i-propoxy, methoxycarbonyl, ethoxycarbonyl, n- or i-propoxycarbohyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N-methyl-N-ethylaminocarbonyl, N-methyl-N-propylaminocarbonyl, N-ethyl-N-propylaminocarbonyl, N-methyl-N-methoxyaminocarbonyl, N,N-diallylaminocarbonyl, N-methyl-N-propargylaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl; or furthermore represents cyclopropyl, cyclopentyl, cyclohexyl or cycloheptyl, in each case optionally mono-, di-, tri-, tetra- or pentasubstituted by identical or different substituents from the group comprising chlorine, methyl and ethyl, or moreover represents a radical

or represents a radical —SO$_2$—R$^7$,

R$^5$ represents hydrogen; or, in the case where R$^4$ represents hydrogen, R$^5$ may also represent a radical

or a radical —SO$_2$—R$^7$, or may represent methyl, ethyl, n- or i-propyl, n-, i-, s- or t-butyl, allyl, butenyl, propargyl or butinyl, in each case optionally mono-, di- or trisubstituted by identical or different substituents, possible substituents in each case being: fluorine, chlorine, bromine, iodine, cyano, nitro, hydroxyl, carboxyl, methoxy, ethoxy, n- or i-propoxy, methoxycarbonyl, ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N-methyl-N-ethylaminocarbonyl, N-methyl-N-propylaminocarbonyl, N-ethyl-N-propylaminocarbonyl, N-methyl-N-methoxyaminocarbonyl, N,N-diallylaminocarbonyl, N-methyl-N-propargylaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl; or furthermore represents cyclopropyl, cyclopentyl, cyclohexyl or cycloheptyl, in each case optionally mono-, di-, tri-, tetra- or pentasubstituted by identical or different substituents from the group comprising chlorine, methyl and ethyl, wherein, in each case, X represents oxygen or sulphur, R$^6$ represents hydrogen, methyl, ethyl, n- or i-propyl, methoxy, ethoxy, methoxymethyl, ethoxymethyl, methoxyethyl, ethoxyethyl, methylthio, ethylthio, methylthiomethyl, methylamino, ethylamino, dimethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, heptafluoro-n-propyl, allyl, propargyl or butenyl, or represents cyclopropyl, cyclopentyl or cyclohexyl, in each case optionally mono-, di-, tri- or tetrasubstituted by identical or different substituents from the group comprising fluorine, chlorine, bromine, methyl and trifluoromethyl, or represents phenyl, phenoxy, phenylthio or phenylamino, in each case optionally mono-, di-or trisubstituted by identical or different substituents from the group comprising chlorine, methyl, methoxy and trifluoromethyl and R$^7$ represents methyl, ethyl, n- or i-propyl, n-, i-, s- or t-butyl, hydroxymethyl, hydroxyethyl, methoxymethyl, methoxyethyl, chloromethyl, dichloromethyl, trifluoromethyl, allyl, butenyl, cyclopropyl, cyclopentyl or cyclohexyl, or represents benzyl or phenyl, in each case optionally mono-, di- or trisubstituted by identical or different substituents, possible substituents in each case being: fluorine, chlorine, bromine, cyano, nitro, methyl, ethyl, methoxy, methylthio and trifluoromethyl, and Ar represents phenyl which is mono-, di-, tri-, tetra- or pentasubstituted by identical or different substituents, or represents 2-pyridyl, 3pyridyl or 4-pyridyl, in each case optionally mono-, di-, tri- or tetrasubstituted by identical or different substituents, possible substituents in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)$_m$—R$^9$, wherein R$^9$ represents amino, methyl, ethyl, methylamino, ethylamino, dimethylamino, diethylamino, fluorodichloromethyl, difluoromethyl, tetrafluoroethyl, trifluorochloroethyl or trifluoromethyl and m represents the number 0, 1 or 2.

The following 1-aryl-5-hydrazino-pyrazoles of the general formula (I) may be mentioned specifically, in addition to the compounds mentioned in the preparation examples:

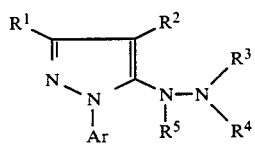

TABLE 1

| R$^1$ | R$^2$ | R$^3$ | R$^4$ | R$^5$ | Ar |
|---|---|---|---|---|---|
| H | NO$_2$ | CH$_3$ | CH$_3$ | H |  |
| H | CN | H | —C(=O)—CH$_3$ | H | 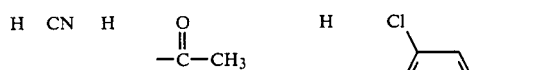 |
| H | CN | H | —SO$_2$—CH$_3$ | H |  |
| H | CN | H | —C(=O)—NH—CH$_3$ | H | 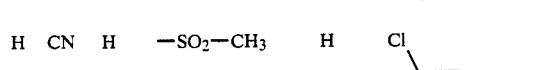 |
| H | CN | H | —C(=O)—CH$_3$ | CH$_3$ |  |

TABLE 1-continued

| R$^1$ | R$^2$ | R$^3$ | R$^4$ | R$^5$ | Ar |
|---|---|---|---|---|---|
| H | CN | H | —C(=O)—C$_2$H$_5$ | CH$_3$ |  |
| H | NO$_2$ | H | CH$_3$ | CH$_3$ | 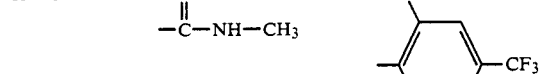 |
| H | NO$_2$ | CH$_3$ | H | H |  |
| H | NO$_2$ | CH$_3$ | —C(=O)—CH$_3$ | H | 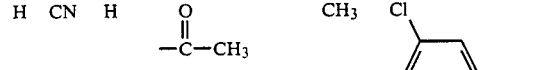 |
| H | NO$_2$ | H | —SO$_2$—CH$_3$ | H |  |

If, for example, 5-chloro-4-cyano-1-(3,5-dichloro-2-pyridyl)-pyrazole and hydrazine hydrate are used as starting substances, the course of the reaction in process (a) according to the invention can be represented by the following equation:

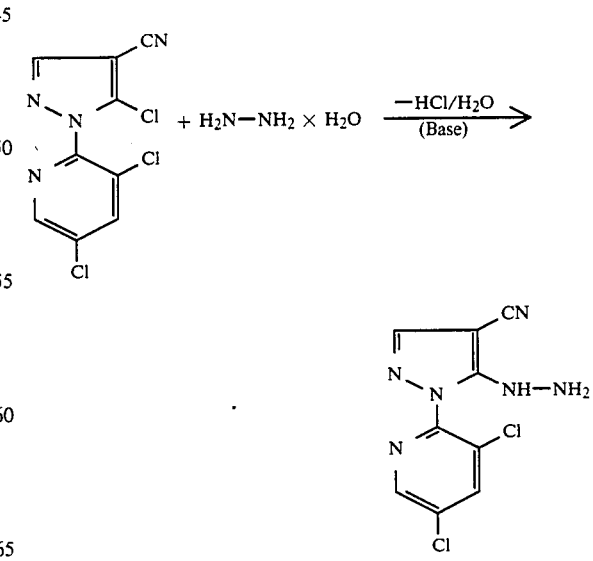

If, for example, 4-cyano-5-(α-methyl-hydrazino)-1-(2,4,6-trichlorophenyl)-pyrazole and ethyl bromoacetate are used as starting substances, the course of the reaction in process (b-α) according to the invention can be represented by the following equation:

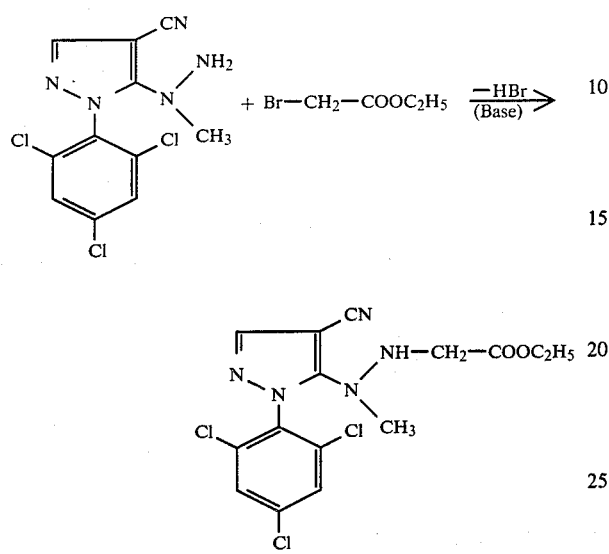

If, for example, 4-cyano-5-hydrazino-1-(2,4-dichlorophenyl)-pyrazole and acetyl chloride are used as starting substances, the course of the reaction in process (b-β) according to the invention can be represented by the following equation:

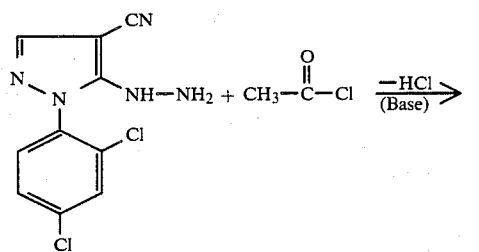

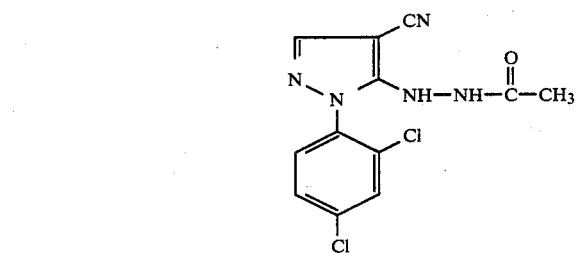

If, for example, 5-hydrazino-3-methyl-4-nitro-1-(2,6-dichloro-4-trifluoromethyl-phenyl)-pyrazole and methyl isocyanate are used as starting substances, the course of the reaction in process (b-γ) according to the invention can be represented by the following equation:

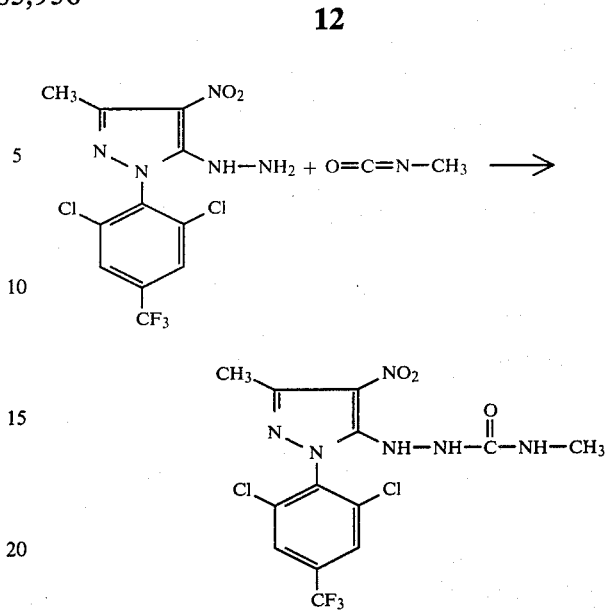

If, for example, 5-hydrazino-4-nitro-1-(2-pyridyl)-pyrazole and methylsulphonyl chloride are used as starting substances, the course of the reaction in process (b-δ) according to the invention can be represented by the following equation:

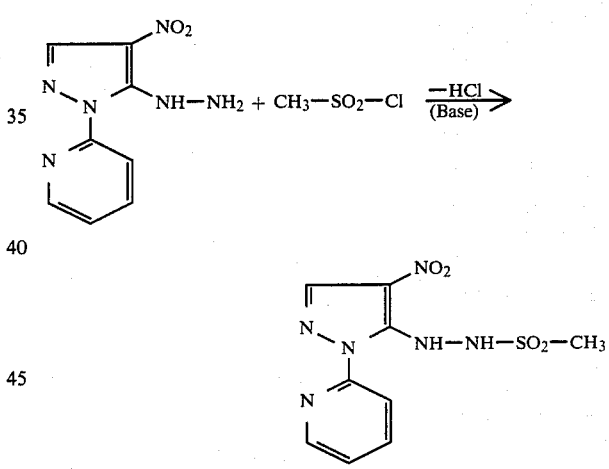

Formula (II) provides a generaly definition of the 1-aryl-5-halogeno-pyrazoles required as starting substances for carrying out process (a) according to the invention. In this formula (II), $R^1$, $R^2$ and Ar preferably represent those radicals which have already been mentioned as preferred for these substituents in connection with the description of the substances of the formula (I) according to the invention.

Hal preferably represents chlorine or bromine.

The 1-aryl-5-halogeno-pyrazoles of the formula (II) are the commonly assigned subject of application Ser. No. 816,643, filed Jan. 6, 1986, now pending, (corresponding to German Pat. No. 3,501,323 of Jan. 17, 1985) and German Pat. No. 3,520,329 of June 7, 1985.

They are obtained, for example, by a process in which 5-amino-1-aryl-pyrazoles of the formula (VIII)

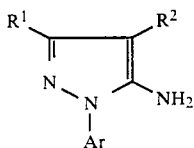

in which

R$^1$, R$^2$ and Ar have the abovementioned meaning, are diazotized with nitrite compounds of the formula (IX)

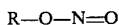

in which

R represents hydrogen or alkyl, or represents an alkali metal cation, in the customary manner in the presence of a hydrogen halide acid, such as, for example, hydrochloric acid or hydrobromic acid, or in the presence of a haloform, such as, for example, chloroform or bromoform, at temperatures between −20° C. and +80° C. (compare, for example, "Organikum" 15th edition VEB Deutscher Verlag der Wissenschaften, Berlin 1981 page 652 et seq.; J. Chem. Soc. C, 1966, 1249 or Rev. Latinoam. Quim. 13, 100-102 3 [1982]).

The 5-amino-1-aryl-pyrazoles of the formula (VIII) are known in some cases (compare, for example, European Pat. No. 26,034, European Pat. No. 53,678 or European Pat. No. 34,945, and DE-OS (German Published Specification) Nos. 3,226,496, 3,408,727 or 3,420,985), and some of them are the subject of commonly assigned application Ser. No. 690,347. filed Jan. 10, 1985, now U.S. Pat. No. 4,614,533 (corresponding to German Pat. No. 3,402,308 of Jan. 24, 1985), German Pat. Nos. 3,520,330 of June 7, and 3,520,327 of June 7, 1985.

They are obtained, for example, by a process in which aryl-hydrazines of the formula (X)

in which

Ar has the abovementioned meaning, are either initially reacted in a 1st stage (α) with acrylonitrile derivatives of the formula (XI)

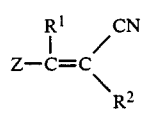

in which

R$^1$ and R$^2$ have the abovementioned meaning and

Z represents halogen, hydroxyl, alkoxy or dialkylamino, or (β) with 2-halogenoacrylonitriles of the formula (XII)

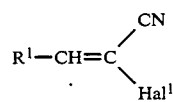

in which

R$^1$ has the abovementioned meaning and

Hal$_1$ represents halogen, in particular chlorine or bromine, if appropriate in the presence of a diluent, such as, for example, glacial acetic acid or ethanol, if appropriate in the presence of a reaction auxiliary, such as, for example, sodium acetate, at temperatures between −20° C. and +20° C., to give the arylhydrazine derivatives of the formula (XIII)

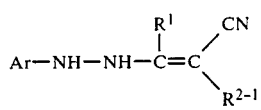

in which

Ar and R$^1$ have the abovementioned meaning and

R$^{2-1}$ represents halogen, cyano or nitro, and these are cyclized in a 2nd stage, if appropriate in the presence of a diluent, such as, for example, ethylene glycol monoethyl ether and, if appropriate, in the presence of an acid catalyst, such as, for example, sulphuric acid or phosphoric acid, at temperatures between +50° C. and +150° C., or are cyclized directly in one reaction step, without isolation of the intermediate stage of the formula (XIII), if appropriate in the presence of a diluent, for example ethylene glycol monoethyl ether or ethanol, at temperatures between +50° C. and +150° C., and, if appropriate, the 5-aminopyrazoles which are unsubstituted in the 4-position and are obtainable by variant (β), of the formula (XIV)

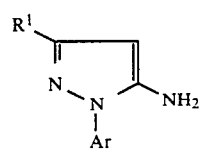

in which

R$^1$ and Ar have the abovementioned meanings, are nitrated in a subsequent reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° C. and +50° C.

If appropriate, it may thereby be advantageous to protect the amino group in the 5-position of the pyrazole ring with the aid of the customary protective group technique, for example by acylation, before the nitration reaction, and to split off the amino protective group again, likewise in a customary manner, for example by hydrolysis with an aqueous or alcoholic base, after the nitration has been carried out.

The arylhydrazines of the formula (X) are known (compare, for example, U.S. Pat. Nos. 4,127,575; 3,609,158; DE-OS (German Published Specification) No. 2,558,399; and J. Chem. Soc. C, 1971, 167-174), or they can be obtained by known processes in a simple analogous manner (compare, for example, Houben-Weyl "Methoden der organischen Chemie" ("Methods of Organic Chemistry") Volume X/2, page 203, Thieme Verlag Stuttgart, 1967), by a procedure in which, for example, the known anilines or pyridylamines of the formula (XV)

in which
Ar has the abovementioned meaning,
are reacted with sodium nitrite in the presence of an acid, such as, for example, sulphuric acid, and the products are then reacted with tin-II chloride, likewise in the presence of an acid, such as, for example, hydrochloric acid, at temperatures between −20° C. and +80° C., or by a procedure in which halogenoaromatics of the formula (XVI)

$$Ar-Hal^2 \qquad (XVI)$$

in which
Ar has the abovementioned meaning and
$Hal_2$ represents halogen, in particular fluorine, chlorine or bromine,
are reacted with hydrazine hydrate, if appropriate in the presence of a diluent, such as, for example, pyridine or dioxane, at temperatures between 0° and 15020 C.

The nitrite compounds of the formula (IX), the acrylonitrile derivatives of the formula (XI), the 2-halogenoacrylonitriles of the formula (XII), the anilines and pyridylamines of the formula (XV) and the halogenoaromatics of the formula (XVI) are generally known compounds of organic chemistry.

Formula (III) provides a general definition of the hydrazine derivatives furthermore required as starting substances for carrying out process (a) according to the invention. In this formula (III), $R^{8-1}$ and $R^{8-2}$ independently of one another in each case preferably represent hydrogen, or represent alkyl, alkenyl or alkinyl with in each case up to 8 carbon atoms and in each case optionally monosubstituted or polysubstituted by identical or different substituents, possible substituents in each case being: halogen, cyano, nitro, hydroxyl, carboxyl, in each case straight-chain or branched alkoxy and alkoxycarbonyl with in each case 1 to 8 carbon atoms in the alkyl part and aminocarbonyl which is optionally substituted by alkyl, alkoxy, alkylsulphonyl, alkenyl or alkinyl with in each case up to 4 carbon atoms, it also being possible for the nitrogen atom of the aminocarbonyl radical to be part of a saturated 3-membered to 7-membered heterocyclic radical, which can optionally also contain 1 or 2 further heteroatoms, in particular nitrogen, oxygen or sulphur; or furthermore represent cycloalkyl which has 3 to 7 carbon atoms and is optionally monosubstituted or polysubstituted by identical or different substituents from the group comprising halogen and/or straight-chain or branched alkyl with 1 to 4 carbon atoms, and $R^{8-1}$ and $R^{8-2}$ independently of one another in each case particularly represent hydrogen, or represent methyl, ethyl, n- or i-propyl, n-, i-, s- or t-butyl, allyl, butenyl, propargyl or butinyl, in each case optionally mono-, di- or trisubstituted by identical or different substituents, possible substituents in each case being: fluorine, chlorine, bromine, iodine, cyano, nitro, hydroxyl, carboxyl, methoxy, ethoxy, n- or i-propoxy, methoxycarbonyl, ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N-methyl-N-ethylaminocarbonyl, N-methyl-N-propylaminocarbonyl, N-ethyl-N-propylaminocarbonyl, N-methyl-N-methoxyaminocarbonyl, N,N-diallylaminocarbonyl, N-methyl-N-propargylaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl, or represent cyclopropyl, cyclopentyl, cyclohexyl or cycloheptyl, in each case optionally mono-, di-, tri-, tetra- or pentasubstituted by identical or different substituents from the group comprising chlorine, methyl and ethyl.

The hydrazine derivatives of the formula (III) are generally known compounds of organic chemistry.

Formula (Ia) or (Ib) provides a general definition of the 5-hydrazino-1-aryl-pyrazoles required as starting substances for carrying out process (b) according to the invention. In this formula (Ia) and (Ib), $R^1$, $R^2$ and Ar preferably represent those radicals which have already been mentioned as preferred for these substituents in connection with the description of the substances of the formula (I) according to the invention.

$R^{8-1}$ and $R^{8-2}$ independently of one another preferably in each case represent those substituents which have already been mentioned for these substituents in connection with the description of the precursors of the formula (III). The 5-hydrazino-1-aryl-pyrazoles of the formulae (Ia) and (Ib) are compounds according to the invention and can be obtained with the aid of process (a) according to the invention.

Formula (IV) provides a general definition of the alkylating agents required as starting substances for carrying out process (b-α) according to the invention. In this formula (IV), $R^{8-3}$ preferably represents alkyl, alkenyl or alkinyl with in each case up to 8 carbon atoms and in each case optionally monosubstituted or polysubstituted by identical or different substituents, possible substituents in each case being: halogen, cyano, nitro, hydroxyl, carboxyl, in each case straight-chain or branched alkoxy and alkoxycarbonyl with in each case 1 to 6 carbon atoms in the alkyl part and aminocarbonyl which is optionally substituted by alkyl, alkoxy, alkylsulphonyl, alkenyl or alkinyl with in each case up to 4 carbon atoms, it also being possible for the nitrogen atom of the aminocarbonyl radical to be part of a saturated 3-membered to 7-membered heterocyclic radical which can optionally also contain 1 or 2 further heteroatoms, in particular nitrogen, oxygen or sulphur; or furthermore represents cycloalkyl which has 3 to 7 carbon atoms and is optionally monosubstituted or polysubstituted by identical or different substituents from the group comprising halogen and/or straight-chain or branched alkyl with 1 to 4 carbon atoms.

$R^{8-3}$ particularly represents methyl, ethyl, n- or i-propyl, n-, i-, s- or t-butyl, allyl, butenyl, propargyl or butinyl, in each case optionally mono-, di- or trisubstituted by identical or different substituents, possible substituents in each case being: fluorine, chlorine, bromine, iodine, cyano, nitro, hydroxyl, carboxyl, methoxy, ethoxy, n- or i-propoxy, methoxycarbonyl ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N-methyl-N-ethylaminocarbonyl, N-methyl-N-propylaminocarbonyl, N-ethyl-N-propylaminocarbonyl, N-methyl-N-methoxyaminocarbonyl, N,N-diallylaminocarbonyl, N-methyl-N-propargylaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl, or represents cyclopropyl, cyclopentyl, cyclohexyl or cycloheptyl, in each case optionally mono, di-, tri-, tetra- or pentasubstituted by identical or different substituents from the group comprising chlorine, methyl and/or ethyl.

A$^1$ preferably represents chlorine, bromine or iodine, or represents p-toluenesulphonyloxy or methoxysulphonyloxy.

The alkylating agents of the formula (IV) are generally known compounds of organic chemistry.

Formula (V) provides a general definition of the acylating agents furthermore required as starting substances for carrying out process (b-$\beta$) according to the invention. In this formula (V), R$^6$ and X preferably represent those radicals which have already been mentioned as preferred for these substituents in connection with the description of the substances of the formula (I) according to the invention.

A$^2$ preferably represents chlorine or bromine, or represents a radical

wherein

R$^6$ has the abovementioned meaning.

The acylating agents of the formula (V) are likewise generally known compounds of organic chemistry.

Formula (VI) provides a general definition of the iso(thio)cyanates furthermore required as starting substances for carrying out process (b-$\gamma$) according to the invention. In this formula (VI), X preferably represents those radicals which have already been mentioned as preferred for this substituent in connection with the description of the substances of the formula (I) according to the invention.

R$^{6-1}$ preferably represents straight-chain or branched alkyl with 1 to 4 carbon atoms, or represents phenyl which is optionally monosubstituted or polysubstituted by identical or different substituents, possible substituents being: halogen and in each case straight-chain or branched alkyl, alkoxy and halogenoalkyl with in each case 1 to 4 carbon atoms and, in the case of the halogenoalkyl, with 1 to 9 identical or different halogen atoms.

R$^{6-1}$ represents, in particular, methyl or ethyl, or represents phenyl which is optionally mono-, di- or trisubstituted by identical or different substituents from the group comprising fluorine, chlorine, methyl, methoxy and trifluoromethyl.

The iso(thio)cyanates of the formula (VI) are likewise generally known compounds of organic chemistry.

Formula (VII) provides a general definition of the sulphonylating agents furthermore required as starting substances for carrying out process (b-$\delta$) according to the invention. In this formula (VII), R$^7$ preferably represents those radicals which have already been mentioned as preferred for these substituents in connection with the description of the substances of the formula (I) according to the invention.

A$^3$ preferably represents chlorine or bromine.

The sulphonylating agents of the formula (VII) are likewise generally known compounds of organic chemistry.

Possible diluents for carrying out process (a) according to the invention are inert organic solvents.

These include, in particular, aliphatic or aromatic hydrocarbons, such as, for example, benzine, benzene, toluene, xylene, petroleum ether, hexane and cyclohexane, or ethers, such as diethyl ether, dioxane, tetrahydrofuran or ethylene glycol dimethyl or diethyl ether.

The reaction temperatures can be varied within a substantial range in carrying out process (c) according to the invention. The reaction is in general carried out at temperatures between 20° C. and 150° C., preferably at temperatures between 50° C. and 120° C.

For carrying out process (a) according to the invention, in general 1.0 to 50.0 moles, preferably 1.0 to 20.0 moles, of hydrazine derivative of the formula (III) are employed per mole of 1-aryl-5-halogeno-pyrazole of the formula (II). Depending on the diluent, reaction temperature, molar ratios, nature of the substituents R$^{8-1}$ and R$^{8-2}$ and general reaction procedure, either $\alpha$-substituted products of the formula (Ia) or $\beta$-substituted products of the formula (Ib) are obtained when substituted hydrazine derivatives of the formula (III) in which R$^{8-1}$ and/or R$^{8-2}$ is/are other than hydrogen are used (compare, for example, Houben-Weyl "Methoden der organischen Chemie" ("Methods of Organic Chemistry") Volume X/2, page 203, Thieme Verlag Stuttgart 1967; compare also the preparation examples). The reaction is carried out and the reaction products of the formula (Ia) or (Ib) are worked up and isolated in the customary manner.

Possible diluents for carrying out processes (b-$\alpha$), (b-$\beta$), (b-$\gamma$) and (b-$\delta$) according to the invention are likewise inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, processes (b-$\alpha$), (b-$\beta$), (b-$\gamma$) and (b-$\delta$) according to the invention are carried out in the presence of an acid-binding agent or a basic reaction auxiliary.

Possible reagents of this type are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a substantial range in carrying out processes (b-$\alpha$), b-$\beta$), (b-$\gamma$) and (b-$\delta$) according to the invention. The reactions are in general carried out at temperatures between −20° C. and +120° C., preferably at temperatures between 0° C. and +100° C.

For carrying out processes (b-$\alpha$), b-$\beta$), (b-$\gamma$) and (b-$\delta$) according to the invention, in general 1.0 to 20.0 moles, preferably 1.0 to 15.0 moles, of alkylating agent of the formula (IV) or of acylating agent of the formula (V) or of iso(thio)cyanate of the formula (VI) or of sulphonylating agent of the formula (VII) and, if appropriate, 1.0 to 3.0 moles, preferably 1.0 to 2.0 moles, of acid-binding agent or basic reaction auxiliary are in general employed per mole of 5-hydrazino-1-aryl-pyrazole of the formula (Ia) or (Ib). The reaction is carried out and the reaction products of the formula (I) are worked up and isolated in the generally customary manner.

In this case also, depending on the diluent, reaction temperature, base, molar ratios, nature of the leaving groups $A^1$, $A^2$ and $A^3$, nature of the participating substituents $R^6$, $R^7$, $R^{8-1}$, $R^{8-2}$ and $R^{8-3}$ and general reaction conditions, different substituent positions result for the hydrogen grouping ($\alpha$- or $\beta$-position) and different degrees of substitution result (mono- or disubstitution) (compare, for example, Synthesis 1983, 157–158). If appropriate, monosubstituted products of the formula (I) can be re-used in a repeated reaction with changed reaction conditions, in order to obtain products with mixed substitution in this manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be employed with particularly good success for combating monocotyledon and dicotyledon weeds in monocotyledon and dicotyledon crops, such as, for example, soybean, cotton or wheat.

When applied in corresponding amounts, the active compounds according to the invention moreover also exhibit an activity as leaf insecticides.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such is sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5 (4H)-one for combating weeds in soy beans.

Mixtures with N,N-dimethyl-N'-(3-trifluoromethylphenyl)-urea; N,N-dimethyl-N'-(3-chloro-4-methylphenyl)urea; N,N-dimethyl-N'-(4-isopropylphenyl)-urea; 4-amino-6-t-butyl-3-ethylthio-1,2,4-triazin-5-(4H)-one; 2,4-dichlorophenoxyacetic acid; 2,4-dichlorophenoxy-propionic acid; (2-methyl-4-chlorophenoxy)-acetic acid; (4-chloro-2-methylphenoxy)-propionic acid; chloroacetic acid N-(methoxymethyl)-2,6-diethylanilide; 2-ethyl-6-methyl-N-(1-methyl-2-methoxyethyl)-chloroacetanilide; 2,6-dinitro-4 -trifluoromethyl-N,N-dipropylaniline; 2-benzyloxyethyl, trimethylsilylmethyl or 2,2-diethoxyethyl 2-[4-(3,5-dichloropyrid-2-yloxy)-phenoxy]-propionate; 2-[1-ethoxyamino)-butylidine]-5-(2-ethylthiopropyl)-1,3-cylcohexanedione; methyl 5-(2,4-dichlorophenoxy)-2-nitrobenzoate; 3,5-diiodo-4-hydroxybenzonitrile; 3-isopropy 1-2,1,3-benzothiadiazin-4-one 2,2-dioxide; 2-chloro-N-{[(4-methoxy-6-methyl-1,3,5-triazin-2-yl)-amino]-carbonyl} benzenesulphonamide; 4-ethylamino-2-t-butylamino-6-methylthio-s-triazine; 2-{4-[<3-chloro-5-(trifluoromethyl)-2-pyridyl>-oxy]-phenoxy}-propanoic acid and propanoic acid ethyl ester; 5-(2-chloro-4-trifluoromethylphenoxy)-2-nitro-benzoic acid; N-(1-ethylpropyl)-3,4-dimethyl-2,6-dinitroaniline; N-methyl-2-(1,3-benzothiazol-2-yloxy)acetanilide; S-(2,3,3-trichloroallyl) N,N-diisopropylthiolcarbamate; and 2-[5-methyl-(1-methylethyl)-4-ox o-2-imidazolin-2-yl]-3-quinolinecarboxylic acid, where appropriate, are also of advantage. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

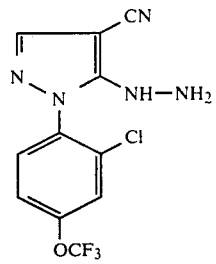

18.3 g (0.05 mole) of 5-bromo-4-cyano-1-(2-chloro-4-trifluoromethoxy-phenyl)-pyrazole and 50 ml (1.0 mole) of hydrazine hydrate are heated under reflux in 300 ml of dioxane for 18 hours. The cooled reaction mixture is concentrated in vacuo, the residue is dissolved in chloroform and the solution is washed successively with water, dilute aqueous hydrochloric acid, aqueous sodium bicarbonate solution and again with water, dried over sodium sulphate and freed from the solvent in vacuo.

9.5 g (60% of theory) of 4-cyano-5-hydrazino-1-(2-chloro-4-trifluoromethoxy-phenyl)-pyrazole of melting point 163° C. (decomposition) are obtained.

PREPARATION OF THE STARTING COMPOUND

EXAMPLE (II-1)

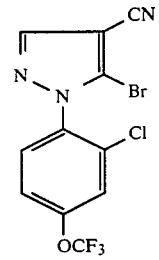

(II-1)

A solution of 3.6 g (0.052 mole) of sodium nitrite in 9 ml of water is added to 9.1 g (0.03 mole) of 5-amino-4-cyano-1-(2-chloro-4-trifluoromethoxy-phenyl)-pyrazole (compare DE-OS (German Published Specification) 3,420,985) in 100 ml of hydrobromic acid at 0° C. to 5° C., with stirring. When the addition has ended, the temperature is allowed to rise to 20° C. and stirring is continued at this temperature for 6 hours; the crystalline product is filtered off with suction and taken up in water, the mixture is neutralized with sodium bicarbonate solution and the product is filtered off with suction and dried.

10 g (91% of theory) of 5-bromo-4-cyano-1-(2-chloro-4-trifluoromethoxy-phenyl)-pyrazole of melting point 83° C. are obtained.

EXAMPLE 2

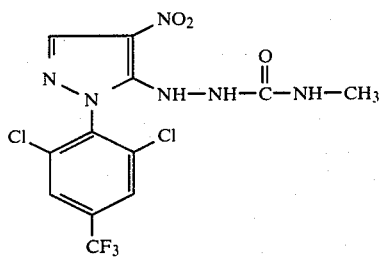

2 drops of triethylamine are added to 11 g (0.03 mole) of 5-hydrazino-4-nitro-1-(2,6-dichloro-4-trifluoromethyl-phenyl)-pyrazole and 2 g (0.035 mole) of methyl isocyanate in 50 ml of ethyl acetate, the mixture is stirred at 20° C. for 12 hours and cooled to 5° C. and the precipitate which has separated out is filtered off with suction.

5 g (40% of theory) of 5-[(β-methylaminocarbonyl)-hydrazino]-4-nitro-1-(2,6-dichloro-4-trifluoromethyl-phenyl)-pyrazole phenyl)-pyrazole of melting point 207° C.–210° C. are obtained.

EXAMPLE 3

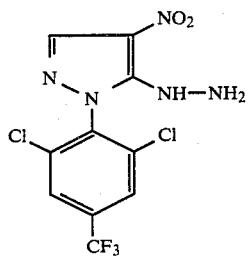

11 g (0.03 mole) of 5-chloro-4-nitro-1-(2,6-dichloro-4-trifluoromethyl-phenyl)-pyrazole and 6 ml (0.12 mole) of hydrazine hydrate in 100 ml of dioxane are left to stand at 20° C. for 16 hours. For working up, the reaction mixture is poured into water and extracted several times with chloroform, the combined organic phases are dried over sodium sulphate and the solvent is removed in vacuo. The residue crystallizes on trituration with ligroin.

8 g (75% of theory) of 5-hydrazino-4-nitro-1-2,6-dichloro-4-trifluoromethyl-phenyl)-pyrazole of melting point 133° C.–135° C. are obtained.

PREPARATION OF THE STARTING COMPOUNDS

EXAMPLE (II-2)

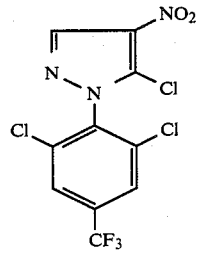
(II-2)

62 g (0.2 mole) of 5-chloro-1-(2,6-dichloro-4-trifluoromethyl-phenyl)-pyrazole are suspended in a mixture of 260 ml of concentrated sulphuric acid and 70 ml of water, and a mixture of 40 ml of concentrated sulphuric acid and 40 ml of concentrated nitric acid is added dropwise at 60° C. When the addition has ended, the mixture is stirred at 60° C. for a further 12 hours, cooled and poured onto ice. The reaction product which separates out as an oil is taken up in toluene and the organic phase is washed several times with water and then with sodium bicarbonate solution and subsequently dried over sodium sulphate. After the solvent has been distilled off in vacuo, the residue is recrystallized from a little petroleum ether.

32 g (44% of theory) of 5-chloro-1-(2,6-dichloro-4-trifluoromethylphenyl)-4-nitro-pyrazole of melting point 80° C.–84° C. are obtained.

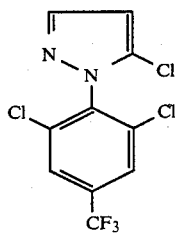

A mixture of 60 g (0.2 mole) of 1-(2,6-dichloro-4-trifluoromethyl-phenyl)-5-hydroxy-pyrazole and 250 ml of phosphorus oxychloride are heated at 160° C. in an autoclave for 20 hours. The cooled reaction mixture is then poured onto ice and the excess phosphorus oxychloride is carefully hydrolyzed with sodium hydroxide solution, while cooling. The precipitate is filtered off with suction, washed several times with water and dried.

32 g (51% of theory) of 5-chloro-1-(2,6-dichloro-4-trifluoromethyl-phenyl)-pyrazole of melting point 70° C.–72° C. are obtained.

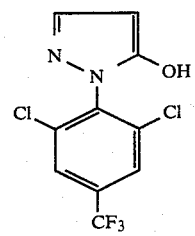

105 g (0.253 mole) of finely powdered diethyl β-(2,6-dichloro-4-trifluoromethyl-phenyl)-hydrazinomethylenemalonate are added in portions to a solution of 30 g (0.75 mole) of sodium hydroxide in 1,000 ml of water at 80°–85° C., with stirring, and the mixture is then stirred at 97°–98° C. for a further 48 hours. The cooled reaction mixture is carefully acidified to pH 2 with concentrated hydrochloric acid and the precipitate thus obtained is filtered off with suction and dried on clay.

100 g (67% of theory) of 5-hydroxy-1-(2,6-dichloro-4-trifluoromethyl-phenyl)-pyrazole of melting point 223° C.–225° C. are obtained.

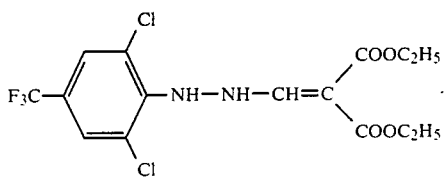

115 g (0.53 mole) of diethyl ethoxymethylenemalonate are added dropwise to a solution of 122.5 g (0.5 mole) of 2,6-dichloro-4-trifluoromethyl-phenylhydrazine in 1,000 ml of ethanol at 70° C.-75° C. in the course of 30 minutes, with stirring, and, when the addition has ended, the mixture is stirred at 70° C. to 75° C. for a further 5 hours. For working up, the solvent is removed in vacuo and the residue is triturated with water, filtered off with suction and dried on clay.

202 g (97% of theory) of diethyl β-(2,6-dichloro-4-trifluoromethylphenyl)-hydrazinomethylene-malonate of melting point 73° C.-83° C. are obtained.

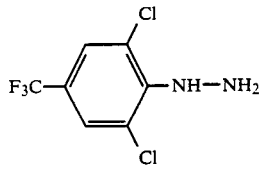

6.2 g (0.025 mole) of 3,4,5-trichloro-trifluoromethylbenzene and 6.25 g (0.125 mole) of hydrazine hydrate are heated under reflux in 12 ml of pyridine at 115°-120° C. for 48 hours. For working up, the solvent is distilled off, the residue is taken up in water and the mixture is extracted three times with in each case about 30 ml of methylene chloride. The combined organic phases are dried over magnesium sulphate, concentrated in vacuo and then distilled.

5.1 g (83% of theory) of 2,6-dichloro-4-trifluoromethylphenylhydrazine of melting point 56° to 57° C. are obtained.

The following 1-aryl-5-hydrazino-pyrazoles of the formula (I) are obtained in a corresponding manner and in accordance with the general statements on the preparation:

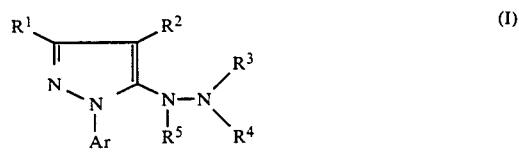

(I)

TABLE 2

| Example No. | $R^1$ | $R^2$ | $R^3$ | $R^4$ | $R^5$ | Ar | Melting point/°C. |
|---|---|---|---|---|---|---|---|
| 4 | H | CN | $C_2H_5-\overset{O}{\underset{\|}{C}}-$ | H | H | N-heterocycle with 2 Cl | 173 |
| 5 | H | $NO_2$ | H | H | H | 2,4,6-trichlorophenyl | 165-170 (decomposition) |
| 6 | H | CN | H | H | H | 2,4-dichlorophenyl | 199-203 |
| 7 | H | CN | H | H | H | 2-Cl-4-$CF_3$-phenyl | 141-145 |
| 8 | H | $NO_2$ | H | H | H | 2-Cl-4-$OCF_3$-phenyl | 169 |

TABLE 2-continued

| Example No. | $R^1$ | $R^2$ | $R^3$ | $R^4$ | $R^5$ | Ar | Melting point/°C. |
|---|---|---|---|---|---|---|---|
| 9 | H | $NO_2$ | $CH_3-\underset{\underset{O}{\|\|}}{C}-$ | H | H | 2,4,6-trichlorophenyl  | 206–208 (decomposition) |
| 10 | H | CN | H | H | H | 3,5-dichloro-2-pyridyl 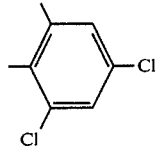 | 216 |
| 11 | H | CN | $CH_3-\underset{\underset{O}{\|\|}}{C}-$ | H | H | 2,4-dichlorophenyl 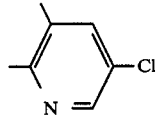 | 90 (decomposition) |
| 12 | H | $NO_2$ | $CH_3-\underset{\underset{O}{\|\|}}{C}-$ | H | H | 2-chloro-4-trifluoromethoxyphenyl  | 168 |
| 13 | H | CN | $CH_3-\underset{\underset{O}{\|\|}}{C}-$ | H | H | 2-chloro-4-trifluoromethylphenyl 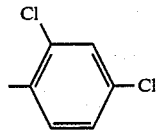 | 208 |
| 14 | H | CN | $CH_3-\underset{\underset{O}{\|\|}}{C}-$ | H | H | 3,5-dichloro-2-pyridyl  | 179–180 |
| 15 | H | CN | $C_2H_5-\underset{\underset{O}{\|\|}}{C}-$ | H | H | 2-chloro-4-trifluoromethylphenyl 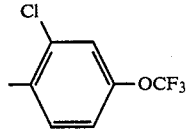 | 203–205 |
| 16 | H | CN | $(CH_3)_2CH-\underset{\underset{O}{\|\|}}{C}-$ | H | H | 2-chloro-4-trifluoromethylphenyl  | 187–189 |
| 17 | $CH_3$ | $NO_2$ | H | H | H | 2,6-dichloro-4-trifluoromethylphenyl 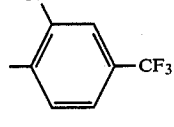 | 178–182 |
| 18 | H | $NO_2$ | $CH_3-\underset{\underset{O}{\|\|}}{C}-$ | H | H | 2,6-dichloro-4-trifluoromethylphenyl  | 205–207 |

TABLE 2-continued

| Example No. | $R^1$ | $R^2$ | $R^3$ | $R^4$ | $R^5$ | Ar | Melting point/°C |
|---|---|---|---|---|---|---|---|
| 19 | H | $NO_2$ | $F_3C-\underset{\underset{O}{\|\|}}{C}-$ | H | H | 2,6-Cl$_2$-4-CF$_3$-phenyl | 88–92 |
| 20 | H | $NO_2$ | $C_2H_5-\underset{\underset{O}{\|\|}}{C}-$ | H | H | 2,6-Cl$_2$-4-CF$_3$-phenyl | 160–162 |
| 21 | H | CN | H | H | $CH_3$ | 2-Cl-4-CF$_3$-phenyl | Oil ($^1$H—NMR: δ 3.25 (s,3H) (CDCl$_3$/TMS) |
| 22 | H | $NO_2$ | H | H | H | 2-Cl-4-CF$_3$-6-Br-phenyl | 80–86 |
| 23 | H | $NO_2$ | $CH_3-\underset{\underset{O}{\|\|}}{C}-$ | H | H | 2-Cl-4-CF$_3$-6-Br-phenyl | 75–105 |
| 24 | H | $NO_2$ | $CH_3-NH-\underset{\underset{S}{\|\|}}{C}-$ | H | H | 2,6-Cl$_2$-4-CF$_3$-phenyl | 182–184 |
| 25 | H | $NO_2$ | $CH_3-SO_2-$ | H | H | 2,6-Cl$_2$-4-CF$_3$-phenyl | 100–120 |
| 26 | H | $NO_2$ | $CH_3-O-\underset{\underset{O}{\|\|}}{C}-$ | H | H | 2,6-Cl$_2$-4-CF$_3$-phenyl | 203–208 |

Use Examples

The compound shown below was employed as the comparison substance in the following use examples:

(A)

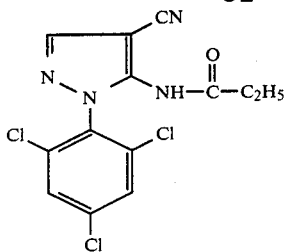

4-Cyano-5-propionamido-1-(2,4,6-trichlorophenyl)-pyrazole (known from DE-OS (German Published Specification) 3,226,513)

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (Like untreated control)
100% = total destruction

In this test, a clearly superior activity and selectivity for useful plants compared with the prior art are shown, for example, by the compounds according to preparation Examples 3 and 18.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (Like untreated control)
100% = total destruction

In this test, a clearly superior selectivity for useful plants compared with the prior art is shown, for example, by the compound according to preparation Example 18.

It will be understood that the specification and examples are illustrative but not limitative of the present invention and that other embodiments within the spirit and scope of the invention will suggest themselves to those skilled in the art.

We claim:
1. A 1-aryl-5-hydrazino-pyrazole of the formula

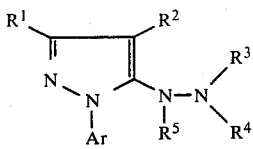

in which
$R^1$ represents hydrogen, or represents straight-chain or branched alkyl with 1 to 4 carbon atoms,
$R^2$ represents cyano or nitro,
$R^3$ represents hydrogen, or represents an alkyl, alkenyl or alkinyl with in each case up to 8 carbon atoms and in each case optionally monosubstituted or polysubstituted by identical or different substituents selected from the group consisting of halogen, cyano, nitro, hydroxyl, carboxyl, in each case straight-chain or branched alkoxy and alkoxy-carbonyl with in each case 1 to 6 carbon atoms in the alkyl part and aminocarbonyl which is optionally substituted by alkyl, alkoxy, alkylsulphonyl, alkenyl or alkinyl with in each case up to 4 carbon atoms, pyrrolidin-1-ylcarbonyl, piperidin-1-ylcarbonyl, morpholin-1-ylcarbonyl, or perhydroazepin-1-yl carbonyl; or furthermore represents cycloalkyl which has 3 to 7 carbon atoms and is optionally monosubstituted or polysubstituted by identical or different substituents from the group consisting of halogen, and/or straight-chain or branched alkyl with 1 to 4 carbon atoms, or represents a radical

or represents a radical $SO_2\text{-}R^7$,
$R^4$ represents hydrogen, or represents alkyl, alkenyl or alkinyl with in each case up to 8 carbon atoms and in each case optionally monosubstituted or polysubstituted by identical or different substituents selected from the group consisting of halogen, cyano, nitro, hydroxyl, carboxyl, in each case straight-chain or branched alkoxy and alkoxycarbonyl with in each case 1 to 6 carbon atoms in the alkyl part and aminocarbonyl which is optionally substituted by alkyl, alkoxy, alkylsulfonyl, alkenyl or alkinyl with in each case up to 4 carbon atoms, pyrrolidin-1-ylcarbonyl, piperidin-1-ylcarbonyl, morpholin-1-ylcarbonyl, or perhydroazepin-1-ylcarbonyl; or furthermore represents cycloalkyl which has 3 to 7 carbon atoms and is optionally monosubstituted or polysubstituted by identical or different substituents from the group consisting of halogen and straight-chain or branched alkyl with 1 to 4 carbon atoms, or represents a radical

or represents a radical $SO_2\text{-}R^7$, $R^5$ represents hydrogen; or, in the case where $R^4$ represents hydrogen, $R^5$ may also represent a radical

or a radical $-SO_2\text{-}R^7$, or may represent alkyl, alkenyl or alkinyl with in each case up to 8 carbon atoms and in each case optionally monosubstituted or polysubstituted by identical or different substituents selected from the group consisting of halogen, cyano, nitro, hydroxyl, carboxyl, in each case straight-chain or branched alkoxy and alkoxycarbonyl with in each case up to 6 carbon atoms in the alky part and amino-carbonyl which is optionally substituted by alkyl, alkoxy, alkylsulphonyl, alkenyl or alkinyl with in each case up to 4 carbon atoms, pyrrolidin-1-ylcarbonyl, piperidin-1-ylcarbonyl, morpholin-1-carbonyl, or perhydroazepin-1-ylcarbonyl; or furthermore represents cycloalkyl which 3 to 7 carbon atoms and is optionally monosubstituted or polysubstituted by identical or different substituents from the group consisting of halogen and/or straight-chain or branched alkyl with 1 to 4 carbon atoms, wherein, in each case, x represents oxygen or sulphur, $R^6$ represents hydrogen, or represents in each case straight-chain or branched alkyl, alkoxy, alkoxyalkyl, alkylthio, alkylthioalkyl, alkylamino or dialkylamino with in each case 1 to 4 carbon atoms in the individual alkyl parts, or represents straight-chain or branched halogenoalkyl with 1 to 4 carbon atoms and 1 to 9 identical or different halogen atoms, or represents in each case straight-chain or branched alkenyl or alkinyl with 2 to 4 carbon atoms, or represents cycloalkyl which has 3 to 7 carbon atoms and is optionally monosubstituted or polysubstituted by identical or different substituents from the group consisting of halogen and in each case straight-chain or branched alkyl with 1 to 4 carbon atoms and halogenoalkyl with 1 to 4 carbon atoms and 1 to 9 identical or different halogen atoms, or represents phenyl, phenoxy, phenylthio or phenylamino, in each case optionally monosubstituted or polysubstituted by identical or different substituents, the phenyl substituents being selected from the group consisting of halogen or in each case straight-chain or branched alkyl or alkoxy, with in each case 1 to 4 carbon atoms, or straight-chain or branched halogenoalkyl with in each case 1 to 4 carbon atoms and 1 to 9 identical or different halogen atoms and $R^7$ represents in each case straight-chain or branched alkyl, hydroxyalkyl or alkoxyalkyl with in each case 1 to 4 carbon atoms in the individual alkyl parts, or represents straight-chain or branched halogenoalkyl with 1 to 4 carbon atoms and 1 to 9 identical or different halogen atoms, or represents in each case straight-chain or branched alkenyl or alkinyl with in each case 2 to 4 carbon atoms, or represents cycloalkyl with 3 to 7 carbon atoms, or represents benzyl or phenyl, in each case optionally monosubstiuted or polysubstituted by identical or different substituents by identical or different substituents from the group consisting of halogen, cyano, nitro and in each case straight-chain or branched alkyl, alkoxy and alkylthio with in each case 1 to 4 carbon alkoxy and alkylthio and straight-chain of branched halogenoalkyl with 1 to 4 carbon atoms and 1 to 9 identical or different halogen atoms and Ar represents phenyl which is monosubstituted or polysubstituted by identical or different substituents, or represents 2-pyridyl, 3-pyridyl or 4-pyridyl, in each case optionally monosubstituted or polysubstituted by identical or different substituents selected from the group consisting of cyano, nitro, halogen, in each case straight-chain or branched alkyl, alkoxy or alkoxy-carbonyl with in each case 1 to 4 carbon atoms in the alkyl part, in each case straight-chain or branched halogenoalkyl or halogenoalkoxy with in each case 1 to 4 carbon atoms and 1 to 9 identical or different halogen atoms and a radical $-S(O)_m\text{-}R^9$, wherein $R^9$ represents amino, or represents in each case straight-chain or branched alkyl, alkylamino or dialkylamino with in each case 1 to 4 carbon atoms in the individual alkyl parts or represents straight chain or branched halogenoalkyl with 1 to 4 carbon atoms and 1 to 9 identical or different halogen atoms and m represents the number 0, 1 or 2.

2. A 1-aryl-5-hydrazino-pyrazole according to claim 1, in which $R^1$ represents hydrogen, methyl, ethyl, n- or i-propyl, or n-, i-, s- or t-butyl, $R^2$ represents cyano or nitro, $R^3$ represents hydrogen, or represents methyl, ethyl, n- or i-propyl, n-, i-, s- or t-butyl, allyl, butenyl, propargyl or butinyl, in each case optionally mono-, di- or trisubstituted by identical or different substituents selected from the group consisting of fluorine, chlorine, bromine, iodine, cyano, nitro, hydroxyl, carboxyl, ethoxy, ethoxy, n- or i-propoxy, methoxycarbonyl, ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N-methyl-N-ethylaminocarbonyl, N-methyl-N-propylaminocarbonyl, N-ethyl-N-propylaminocarbonyl, N-methyl-N-methoxyaminocarbonyl, N,N-diallylaminocarbonyl, N-methyl-N-propargylaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl; or furthermore represents cyclopropyl, cyclopentyl, cyclohexyl or cycloheptyl, in each case optionally mono-, di-, tri-, tetra- or pentasubstituted by identical or different substituents from the group ine, methyl or ethyl, or represents a radical

or represents a radical $-SO_2-R^7$, $R^4$ represents hydrogen, or represents methyl, ethyl, n- or i-propyl, n-, i-, s- or t-butyl, allyl, butenyl, propargyl or butinyl, in each case optionally mono-, di- or trisubstituted by identical or different substituents selected from the group consisting of fluorine, chlorine bromine, iodine, cyano, nitro, hydroxyl, carboxyl, methoxy, ethoxy, n- or i-propoxy, methoxycarbonyl, ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N-methyl-N-ethylaminocarbonyl, N-methyl-N-propylaminocarbonyl, N-ethyl-N-propylaminocarbonyl, N-methyl-N-methoxyaminocarbonyl, N,N-diallylaminocarbonyl, N-methyl-N-propargylaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl; or furthermore represents cyclopropyl, cyclopentyl, cyclohexyl or cycloheptyl, in each case optionally mono-, di-, tri-, tetra- or pentasubstituted by identical or different substituents from the group rine, methyl and ethyl, or moreover represents a radical

or represents a radical —$SO_2$—$R^7$,
$R^5$ represents hydrogen; or, in the case where
$R^4$ represents hydrogen, $R^5$ may also represent a radical

or a radical —$SO_2$—$R^7$, or may represent methyl, ethyl, n- or i-propyl, n-, i-, s- or t-butyl, allyl, butenyl, propargyl or butinyl, in each case optionally mono-, di- or trisubstituted by identical or different substituents selected from the group consisting of fluorine, chlorine, bromine, iodine, cyano, nitro, hydroxyl, carboxyl, methoxy, ethoxy, n- or i-propoxy, methoxycarbonyl, ethoxycarbonyl, n- or i-propoxycarbonyl, n-, i-, s- or t-butoxycarbonyl, aminocarbonyl, N-methylaminocarbonyl, N-ethylaminocarbonyl, N,N-dimethylaminocarbonyl, N,N-diethylaminocarbonyl, N-methyl-N-ethylaminocarbonyl, N-methyl-N-propylaminocarbonyl, N-ethyl-N-propylaminocarbonyl, N-methyl-N-methoxyaminocarbonyl, N,N-diallylaminocarbonyl, N-methyl-N-propargylaminocarbonyl, N-methylsulphonylaminocarbonyl, N-ethylsulphonylaminocarbonyl, pyrrolidin-1-ylcarbonyl, piperidin-1-ylcarbonyl, morpholin-4-ylcarbonyl and perhydroazepin-1-ylcarbonyl; or furthermore represents cyclopropyl, cyclopentyl, cyclohexyl or cycloheptyl, in each case optionally mono-, di-, tri-, tetra- or penta/substituted by identical or different substituents from the group consisting of chlorine, methyl and ethyl,
wherein, in each case,
X represents oxygen or sulphur,
$R^6$ represents hydrogen, methyl, ethyl, n- or i-propyl, methoxy, ethoxy, methoxymethyl, ethoxymethyl, methoxyethyl, ethoxyethyl, methylthio, ethylthio, methylthiomethyl, ethylthiomethyl, methylamino, ethylamino, di-methylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, heptafluoro-n-propyl, allyl, propargyl or butenyl, or represents cyclopropyl, cyclopentyl or cyclohexyl, in each case optionally mono-, di-, tri- or tetrasubstituted by identical or different substituents from the group consisting of fluorine, chlorine, bromine, methyl and trifluoromethyl, or represents phenyl, phenoxy, phenylthio or phenylamino, in each case optionally mono-, di- or trisubstituted by identical or different substituents from the group consisting of chlorine, methyl, methoxy and trifluoromethyl and $R^7$ represents methyl, ethyl, n- or i-propyl, n-, i-, s- or t-butyl, hydroxymethyl, hydroxyethyl, methoxymethyl, methoxyethyl, chloromethyl, dichloromethyl, trifluoromethyl, allyl, butenyl, cyclopropyl, cyclopentyl or cyclohexyl, or represents benzyl or phenyl, in each case optionally mono-, di- or trisubstituted by identical or different substituents, selected from the group consisting of fluorine, chlorine, bromine, cyano, nitro, methyl, ethyl, methoxy, methylthio and trifluoromethyl, and Ar represents phenyl which is mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents selected from the group consisting of cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —$S(O)_m$—$R^9$,
wherein
$R^9$ represents amino, methyl, ethyl, methylamino, ethylamino, dimethylamino, diethylamino, fluorodichloromethyl, difluoromethyl, tetrafluoroethyl, trifluorochloroethyl or trifluoromethyl and m represents the number 0, 1 or 2.

3. A compound according to claim 1 wherein such compound is 5-hydrazino-4-nitro-1-(2,6-dichloro-4-trifluoromethylphenyl)-pyrazole of the formula

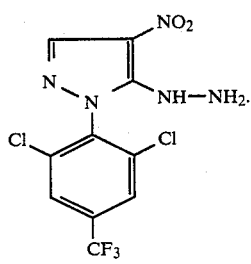

4. A compound according to claim 1, wherein such compound is 5-[(β-acetyl)-hydrazino]-4-nitro-1-(2,6-dichloro-4-trifluoromethyl-phenyl)-pyrazole of the formula

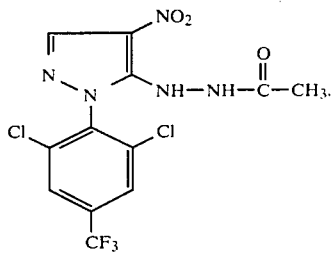

5. A herbicidal composition comprising a herbicidally effective amount of a 1-aryl-5 hydrazino-pyrazole according to claim 1 in admixture with a diluent.

6. A method of combating unwanted vegetation which comprises applying to such vegetation or to a locus from which it is desired to exclude such vegetation a herbicidally effective amount of a 1-aryl-5-hydrazinopyrazole according to claim 1.

7. The method according to claim 6, wherein such compound is
   5-hydrazino-4-nitro-1-(2,6-dichloro-4-trifluoromethyl-phenyl)-pyrazole or
   5-[(β-acetyl)-hydrazino]-4-nitro-1-(2,6-dichloro-4-trifluoromethyl-phenyl)-pyrazole.

* * * * *

UNITED STATES PATENT AND TRADEMARK OFFICE
CERTIFICATE OF CORRECTION

PATENT NO. : 4,685,956

DATED : August 11, 1987

INVENTOR(S) : Reinhold Gehring, et al.

It is certified that error appears in the above-identified patent and that said Letters Patent is hereby corrected as shown below:

| | |
|---|---|
| Col. 6, line 43 | After "4" insert -- - -- |
| Col. 7, line 41 | Correct spelling of --i-propoxy-carbonyl-- |
| Col. 8, line 64 | After "3" insert -- - -- |
| Col. 14, line 1 | Delete "Hal$_1$" and substitute --Hal$_2^1$-- |
| Col. 15, line 15 | Delete "Hal$_2^1$" and substitute --Hal$^2$-- |
| Col. 15, line 19 | Delete "15020C." and substitute --150°C.-- |
| Col. 20, line 43 | Delete "is" and substitute --as-- |
| Col. 21, line 28 | Correct spelling of --butylidene-- |
| Col. 21, line 30 | Delete "3-isopropy 1-2,1,3" and substitute --3-isopropyl-2,1,3- -- |
| Col. 21, line 42 | Delete "ox o" and substitute --oxo-- |
| Col. 23, line 23 | After "phenyl)-pyrazole" first instance delete "phenyl)-pyrazole" |
| Col. 23, line 48 | After "4-nitro-1'" insert --(-- |
| Col. 32, line 35 | Delete "-yl carbonyl" and substitute -- -ylcarbonyl -- |
| Col. 33, line 31 | Delete "x" and substitute --X-- |
| Col. 34, lines 1-2 | Delete "by identical or different substituents" second instance |
| Col. 34, line 5 | After "carbon" delete "alkoxy and alkylthio" and insert --atoms-- |
| Col. 34, line 6 | Delete "of" and substitute --or-- |

UNITED STATES PATENT AND TRADEMARK OFFICE
CERTIFICATE OF CORRECTION

PATENT NO. : 4,685,956

DATED : August 11, 1987

INVENTOR(S) : Reinhold Gehring, et al.

It is certified that error appears in the above-identified patent and that said Letters Patent is hereby corrected as shown below:

Col. 34, line 42        Delete "ethoxy" first instance and substitute --methoxy--

Col. 35, line 60        Correct --pentasubstituted--

Signed and Sealed this

Thirty-first Day of May, 1988

Attest:

DONALD J. QUIGG

Attesting Officer        Commissioner of Patents and Trademarks